US008524104B1

(12) United States Patent
Michael

(10) Patent No.: US 8,524,104 B1
(45) Date of Patent: Sep. 3, 2013

(54) FLUOROALKENYL SULFATE SURFACTANTS

(75) Inventor: Jeffrey D. Michael, Marinette, WI (US)

(73) Assignee: Ansul, Incorporated, Marinette, WI (US)

( * ) Notice: Subject to any disclaimer, the term of this patent is extended or adjusted under 35 U.S.C. 154(b) by 1018 days.

(21) Appl. No.: 12/548,530

(22) Filed: Aug. 27, 2009

Related U.S. Application Data

(60) Provisional application No. 61/190,403, filed on Aug. 28, 2008.

(51) Int. Cl.
*A62D 1/00* (2006.01)
*A62D 1/02* (2006.01)
*A62D 1/08* (2006.01)
*A62C 3/00* (2006.01)
*A62C 31/00* (2006.01)
*A62C 13/00* (2006.01)
*C07C 21/18* (2006.01)

(52) U.S. Cl.
USPC ....... 252/2; 252/3; 252/8; 252/8.05; 252/601; 252/610; 570/123; 570/124; 570/142; 570/153; 570/155; 570/172

(58) Field of Classification Search
USPC ................. 570/123, 124, 142, 153, 155, 172; 252/2, 3, 8, 8.05, 601, 610
See application file for complete search history.

(56) References Cited

U.S. PATENT DOCUMENTS 2,559,751 A 7/1951 Berry et al.
3,145,222 A 8/1964 Brace
3,258,423 A 6/1966 Tuve et al.
3,395,170 A 7/1968 Walts et al.
3,772,195 A 11/1973 Francen
3,952,075 A 4/1976 Nakamura et al.
4,014,926 A 3/1977 Dear et al.
4,059,613 A 11/1977 Nakamura et al.
4,435,330 A 3/1984 Falk
4,536,298 A 8/1985 Kamei et al.
4,795,590 A 1/1989 Kent et al.
5,085,786 A 2/1992 Alm et al.
5,207,932 A 5/1993 Norman et al.
5,218,021 A * 6/1993 Clark et al. .................... 524/56
5,296,627 A 3/1994 Tang et al.
5,585,517 A 12/1996 Deisenroth et al.
5,616,273 A 4/1997 Clark et al.
5,750,043 A 5/1998 Clark
5,833,874 A * 11/1998 Stewart et al. ................... 252/8
5,904,933 A * 5/1999 Riess et al. .................... 424/450
5,980,936 A * 11/1999 Krafft et al. .................. 424/450
6,365,769 B1 4/2002 Behr et al.
6,436,306 B1 8/2002 Jennings
6,706,923 B2 3/2004 Haniff et al.
2008/0051312 A1* 2/2008 Lestage et al. ................ 510/475
2008/0149878 A1* 6/2008 Kirsch et al. ...................... 252/2
2009/0312432 A1* 12/2009 Hierse et al. ................. 514/628

FOREIGN PATENT DOCUMENTS

CA 983929 2/1976
DE 111522 2/1975
JP 50121179 9/1975
JP 03032889 A 2/1991
JP 06011792 A 1/1994
WO WO 93/07123 4/1993
WO WO 03/010128 A2 2/2003

OTHER PUBLICATIONS

EICsearch.pdf 1700-search (Mar. 20, 2013).*
Brace, Neal O.; "Some Approaches to the Synthesis of Fluorinated Alcohols and Esters. II. Use of F-Alkyl Iodides for the Synthesis of F-Alkyl Alkanols"; Journal of Fluorine Chemistry, 20 (1982), pp. 313-327.
Brace, Neal O.; "Syntheses with perfluoroalkyl radicals from perfluoroalkyl iodides. A rapid survey of synthetic possibilities with emphasis on practical applications. Part one: alkenes, alkynes and allylic compounds"; Journal of Fluorine Chemistry 93 (1999), pp. 1-25.
Burwell, Jr., Robert L.; "The Hydrolysis of Optically Active Secondary Butyl Hydrogen Sulfate"; Journal of Am. Chem. Soc.; Chemical Laboratory of Northwestern University; vol. 74; (Mar. 20, 1952), pp. 1462-1466.
Burwell, Jr., Robert L.; "The Stereochemistry of the Sulfation of Optically Active Secondary Butyl Alcohol"; Journal of Am. Chem. Soc.; Chemical Laboratory of Northwestern University; (May 1949), pp. 1769-1771.
Calhoun, George M. and Burwell, Jr., Robert L. "The Hydrolysis of Sodium Alkyl Sulfates in Basic Aqueous Solution"; Journal of Am. Chem. Soc.; vol. 77, (Dec. 20, 1955), pp. 6441-6445.
Dolbier, Jr., William R. "Structure, Reactivity, and Chemistry of Fluoroalkyl Radicals"; Chem. Rev. 1996, 96. pp. 1557-1584.
K. Nakano, Kogyo Kagaku Zasshi, 69: 1163 (1966).
Kissa, Erik. "Fluorinated Surfactants"; Marcel Dekker, Inc. (1994), Chapter 2, pp. 46 and 65.

* cited by examiner

*Primary Examiner* — Joseph D Anthony

(57) ABSTRACT

Fire extinguishing compositions and methods of extinguishing a fire comprising compounds of formula (I) where $R_f$ is a fluorocarbon group. The compounds and compositions described herein are useful as intermediates in the preparation of or as additives to AFFF (aqueous film forming foam) formulations used for the extinguishment of fuel and solvent fires.

16 Claims, No Drawings

FLUOROALKENYL SULFATE SURFACTANTS

CROSS-REFERENCE TO RELATED APPLICATIONS

The present patent application claims the benefit of the filing date under 35 U.S.C. §119(e) of Provisional U.S. Patent Application No. 61/190,403, filed Aug. 28, 2008, which is hereby incorporated by reference.

TECHNICAL FIELD

This disclosure relates to fluorinated compounds, fire extinguishing compositions comprising fluorinated compounds, and to methods for extinguishing, controlling, or preventing fires by using such compositions. It particularly relates to fluoroalkenyl sulfate surfactants.

BACKGROUND

Firefighting foam concentrates are mixtures of foaming agents, solvents and other additives. These concentrates are intended to be mixed with water, the resulting solution foamed by mechanical means, and the foam projected onto the surface of a burning liquid. A particular class of firefighting foam concentrates is known as an aqueous film-forming foam (AFFF). AFFF concentrates have the quality of being able to spread an aqueous film on the surface of hydrocarbon liquids, enhancing the speed of extinguishment of fuel and solvent fires. Surfactants added to AFFF lower surface tension values which permits the foam to spread on the surface of the hydrocarbon liquids.

Aqueous film-forming foams provide a blanket to cover the fuel surface excluding air preventing further ignition of the fuel. For this reason aqueous film-forming foam compositions are particularly desirable for extinguishing fires involving flammable fuels, such as gasoline, naphtha, diesel oils, hydraulic fluids and other hydrocarbons.

Aqueous film-forming foams typically include a surfactant to impart important film forming properties that are useful in the extinguishment of burning liquids. Commonly used anionic hydrocarbon surfactants include alkyl ether sulfates and alpha olefin sulfates. What is needed are fluorinated sulfate surfactants which can enhance the fire extinguishment properties and stability of firefighting foams, including reducing surface tension and improving foam expansion.

BRIEF SUMMARY

The present invention is directed to fluoroalkenyl sulfate compositions thereof, as well as methods of making these compositions.

In a first aspect, the present invention relates to compounds of formula (I):

$$[R_f—\equiv—CH_2—O—L—SO_3^-]_xM \quad (I)$$

where L is absent, $C_1$-$C_{10}$ alkylene-O—, $(—CH_2CH_2O—)_n$, $(—CH_2CH(CH_3)O—)_n$, or $(—CH_2CH(OH)CH_2O—)_n$; n is an integer from 1 to 10; $R_f$ is a $C_4$-$C_{10}$ alkyl group substituted with 2m or (2m+1) fluoro atoms where m is the number of carbons in the alkyl backbone; M is an alkali metal cation, an alkaline earth metal cation, ammonium cation, a $C_1$-$C_4$ mono-substituted ammonium cation, a $C_1$-$C_4$ di-substituted ammonium cation, a $C_1$-$C_4$ tri-substituted ammonium cation, or a $C_1$-$C_4$ tetra-substituted ammonium cation; and x is an integer selected from 1 or 2, and corresponds to the valency of M. In certain embodiments, M is an alkali metal cation selected from the group consisting of a potassium, lithium, or sodium cation, and x is 1. In other embodiments, M is a magnesium cation, and x is 2.

In a second aspect, the present invention relates to fire extinguishing compositions comprising: at least one solvent; and a first fluorosurfactant of formula (I)

$$[R_f—\equiv—CH_2—O—L—SO_3^-]_xM \quad (I)$$

where

- L is absent, $C_1$-$C_{10}$ alkylene-O—, $(—CH_2CH_2O—)_n$, $(—CH_2CH(CH_3)O—)_n$, or $(—CH_2CH(OH)CH_2O—)_n$;
- n is an integer from 1 to 10;
- $R_f$ is a $C_4$-$C_{10}$ alkyl group substituted with 2m or (2m+1) fluoro atoms where m is the number of carbons in the alkyl backbone;
- M is an alkali metal cation, an alkaline earth metal cation, ammonium cation, a $C_1$-$C_4$ mono-substituted ammonium cation, a $C_1$-$C_4$ di-substituted ammonium cation, a $C_1$-$C_4$ tri-substituted ammonium cation, or a $C_1$-$C_4$ tetra-substituted ammonium cation; and x is an integer selected from 1 or 2, and corresponds to the valency of M. In certain embodiments, the compositions further comprise a hydrocarbon surfactant; and a second fluorosurfactant. In certain embodiments, the solvent is selected from the group consisting of water, iso-propyl alcohol, t-butyl alcohol, glycol, butyl carbitol, and hexylene glycol.

In a third aspect, the present invention relates to methods of extinguishing a fire comprising: applying to said fire a composition comprising: at least one solvent; and a compound of formula I $$[R_f—\equiv—CH_2—O—L—SO_3^-]_xM \quad (I)$$

where

- L is absent, $C_1$-$C_{10}$ alkylene-O—, $(—CH_2CH_2O—)_n$, $(—CH_2CH(CH_3)O—)_n$, or $(—CH_2CH(OH)CH_2O—)_n$;
- n is an integer from 1 to 10;
- $R_f$ is a $C_4$-$C_{10}$ alkyl group substituted with 2m or (2m+1) fluoro atoms where m is the number of carbons in the alkyl backbone;
- M is an alkali metal cation, an alkaline earth metal cation, ammonium cation, a $C_1$-$C_4$ mono-substituted ammonium cation, a $C_1$-$C_4$ di-substituted ammonium cation, a $C_1$-$C_4$ tri-substituted ammonium cation, or a $C_1$-$C_4$ tetra-substituted ammonium cation; and x is an integer selected from 1 or 2, and corresponds to the valency of M. In certain embodiments, the composition can further comprise a hydrocarbon surfactant; and a second fluorosurfactant.

In a fourth aspect, the present invention relates to methods for preparing a compound of formula (I)

$$R_f—\equiv—CH_2—O—L—SO_3^- \quad (I)$$

where L is absent, $C_1$-$C_{10}$ alkylene-O—, $(—CH_2CH_2O—)_n$, $(—CH_2CH(CH_3)O—)_n$, or $(—CH_2CH(OH)CH_2O—)_n$; n is an integer from 1 to 10;

$R_f$ is a $C_4$-$C_{10}$ alkyl substituted with 2m or (2m+1) fluoro atoms where m is the number of carbons in the alkyl backbone comprising:

reacting a compound of formula II $$H—\equiv—CH_2—O—L—SO_3^- \quad (II)$$

with a compound of formula III: $R_f$—I (III), in the presence of a radical initiator, followed by the addition of a strong base, to form a compound of formula (I). In certain embodiments, the radical initiator is 2,2'-azobis-2-methylpropionitrile, CuCl, dithionite thiourea dioxide, or sodium hydroxymethane sulfinate.

In a fifth aspect, the present invention relates to compounds of formula (II):

$$[H—\equiv—CH_2—O—L—SO_3^-]_xM \quad (II)$$

where L is $C_1$-$C_{10}$ alkylene-O—, $(—CH_2CH_2O—)_n$, $(—CH_2CH(CH_3)O—)_n$, or $(—CH_2CH(OH)CH_2O—)_n$; n is an integer from 1 to 10; M is an alkali metal cation, an alkaline earth cation, an ammonium cation, a $C_1$-$C_4$ mono-substituted ammonium cation, a $C_1$-$C_4$ di-substituted ammonium cation, a $C_1$-$C_4$ tri-substituted ammonium cation, or a $C_1$-$C_4$ tetra-substituted ammonium cation; and x is an integer selected from 1 or 2 that corresponds to the valency of M.

DETAILED DESCRIPTION

The present invention relates to fluoroalkenyl sulfates, intermediates in the synthesis thereof, including alkenyl sulfates, and fire extinguishing compositions and methods of extinguishing a fire comprising fluoroalkenyl sulfates. Fluoroalkenyl sulfates have been found to be useful additives to AFFF (aqueous film forming foam) formulations used for the extinguishment of fuel and solvent fires. These compounds are a type of ionic fluorosurfactant and as such provide the useful properties of low surface tension, aqueous film formation, and fuel vapor suppression.

ABBREVIATIONS AND DEFINITIONS

When describing the compounds, compositions, methods and processes of this invention, the following terms have the following meanings, unless otherwise indicated.

"The term "alkyl group" or "alkyl" includes straight and branched carbon chain radicals. The term "alkylene" refers to a diradical of an unsubstituted or substituted alkane. For example, a "$C_{1-6}$ alkyl" is an alkyl group having from 1 to 6 carbon atoms. Examples of $C_1$-$C_6$ straight-chain alkyl groups include, but are not limited to, methyl, ethyl, n-propyl, n-butyl, n-pentyl, and n-hexyl. Examples of branched-chain alkyl groups include, but are not limited to, isopropyl, tert-butyl, isobutyl, etc. Examples of alkylene groups include, but are not limited to, $—CH_2—$, $—CH_2—CH_2—$, $—CH_2—CH(CH_3)—CH_2—$, and $—(CH_2)_{1-3}$. Alkyl groups can be substituted or unsubstituted, unless otherwise indicated. Examples of substituted alkyl include haloalkyl, thioalkyl, aminoalkyl, and the like. Alkylene groups can be substituted or unsubstituted, unless otherwise indicated.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

It will be apparent to one skilled in the art that certain compounds of the present invention may exist in tautomeric forms, all such tautomeric forms of the compounds being within the scope of the invention. Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

An "alkali metal cation" is a positively charged ion of an alkali metal. Examples of alkali metals include lithium (Li), sodium (Na), potassium (K), rubidium (Rb), cesium (Cs), and francium (Fr). In particular embodiments, alkali metal cations include cations of lithium, sodium, and potassium.

An "alkaline earth metal cation" is a positively charged ion of an alkaline earth metal. Examples of alkaline earth metals include beryllium (Be), magnesium (Mg), calcium (Ca), strontium (Sr), barium (Ba) and radium (Ra). In particular embodiments, alkaline earth metal cations include cations of magnesium and calcium.

An "ammonium cation" is $NH_4^+$.

A $C_1$-$C_4$ mono-substituted ammonium cation is an ammonium cation that is mono-substituted with a $C_1$-$C_4$ alkyl such as methylammonium, ethylammonium, i-propylammonium, n-propylammonium, n-butylammonium, i-butylammonium, sec-butylammonium, and t-butylammonium.

A $C_1$-$C_4$ di-substituted ammonium cation is an ammonium cation that is di-substituted with a $C_1$-$C_4$ alkyl such as dimethylammonium, di-ethylammonium, di-1-propylammonium, di-n-propylammonium, and di-n-butylammonium.

A $C_1$-$C_4$ tri-substituted ammonium cation is an ammonium cation that is tri-substituted with a $C_1$-$C_4$ alkyl such as trimethylammonium, tri-ethylammonium, and tri-n-butylammonium.

A $C_1$-$C_4$ tetra-substituted ammonium cation is an ammonium cation that is tetra-substituted with a $C_1$-$C_4$ alkyl such as tetra-methylammonium, tetra-ethylammonium, and tetra-butylammonium.

Compounds

In one embodiment, compounds of formula (I) are provided:

$$[R_f—\equiv—CH_2—O—L—SO_3^-]_xM \quad (I)$$

where

- L is absent, $C_1$-$C_{10}$alkylene-O—, $(—CH_2CH_2O—)_n$, $(—CH_2CH(CH_3)O—)_n$, or $(—CH_2CH(OH)CH_2O—)_n$;
- n is an integer from 1 to 10;
- $R_f$ is a $C_4$-$C_{10}$ alkyl group substituted with 2m or (2m+1) fluoro atoms where m is the number of carbons in the alkyl backbone;
- M is an alkali metal cation, an alkaline earth metal cation, ammonium cation, a $C_1$-$C_4$ mono-substituted ammonium cation, a $C_1$-$C_4$ di-substituted ammonium cation, a $C_1$-$C_4$ tri-substituted ammonium cation, or a $C_1$-$C_4$ tetra-substituted ammonium cation; and
- x is an integer selected from 1 or 2, and corresponds to the valency of M.
- $R_f$ for the compounds of formula I is a $C_4$-$C_{10}$ alkyl group substituted with 2m or (2m+1) fluoro atoms where m is the number of carbons in the alkyl backbone. Therefore for a $C_4$ alkyl group, m is 4. Accordingly, a $C_4$ alkyl group can be substituted with 8 fluoro groups (2m) which would be a $C_4F_8$ group or with 9 fluoro groups (2m+1) which would be a $C_4F_9$ group.

Compositions

In one embodiment, fire extinguishing compositions are provided. The compositions comprise at least one solvent, and a compound of formula (I).

The term "composition" as used herein is intended to encompass a product comprising the specified ingredients in the specified amounts, as well as any product which results, directly or indirectly, from combination of the specified ingredients in the specified amounts.

The compositions may be foams, including AFFF (aqueous film forming foam) formulations or concentrates used for the extinguishment of fuel and solvent fires. Concentrates upon dilution with water and aeration, produce a foam.

Preferably, the compositions include a fluoroalkenyl sulfate component. More preferably, the compositions include an amount of fluoroalkenyl sulfate effective to provide desired surfactant properties to the composition.

The compositions may be provided in the form of solutions, dispersions, gels, emulsions and microemulsions in at least one solvent. The solvent can be water, a water miscible solvent, or combination thereof. Water miscible solvents include, for example, alcohols (for example, ethanol, propanol, iso-propyl alcohol, t-butyl alcohol); glycols (for example, ethylene glycol, propylene glycol, 1,4-butanediol); and glycol derivatives (for example butyl carbitol also known as diethylene glycol monobutyl ether, and dipropylene glycol monobutyl ether). Examples of suitable solvents include water, iso-propyl alcohol, t-butyl alcohol, glycol, butyl carbitol, and hexylene glycol.

In some aspects, the composition may comprise a hydrocarbon surfactant. The term hydrocarbon surfactants as used herein refers to surfactants which are non-fluorinated surfactants and comprise a hydrophobic group and hydrophilic group. Hydrocarbon surfactants may be ionic (anionic, cationic, amphoteric) or nonionic. Hydrocarbon surfactants are known to one skilled in the art, including but not limited to those disclosed in U.S. Pat. Nos. 4,795,590; 3,772,195; 5,207,932; 6,436,306. Any suitable hydrocarbon surfactant known to one skilled in the art may be used in the compositions. Amphoteric hydrocarbon surfactants include those comprising amino and carboxy groups, and those comprising amino and sulfo groups. Nonionic hydrocarbon surfactants include polyoxyethylene derivatives of alkyl phenols, linear or branched alcohols, fatty acids, alkyl polyglycosides, and block copolymers containing polyoxyethylene and polyoxypropylene units. Other examples of hydrocarbon surfactants include for example, sodium laureth sulfate, also known as sodium lauryl ether sulfate (SLES); polyoxyethylene ether alcohol; dioctyl sodium sulfosuccinate; ammonium alkyl phenoxy polyoxyethylene sulfate; alkyl ether sulfate surfactants In other aspects, the composition may comprise another fluorosurfactant in addition to the compounds described above, such as the fluoroalkenyl sulfate of formula (I). The term fluorosurfactants as used herein refers to surfactants which are fluorinated and comprise a hydrophobic group and hydrophilic group. Fluorosurfactants may be ionic (anionic, cationic, amphoteric) or nonionic. Fluorosurfactants are known to one skilled in the art, including but not limited to those disclosed in U.S. Pat. Nos. 3,258,423; 4,536,298; 4,795,590; and 5,085,786. In other aspects, the composition may comprise a fluorocarbon polymer. Fluorocarbon polymers are known to one skilled in the art and include, but are not limited to, those disclosed in U.S. Pat. Nos. 5,616,273; 5,750,043, and 5,218,021. In other aspects, the composition may comprise a first fluorosurfactant of formula (I), a hydrocarbon surfactant, and a second fluorosurfactant.

The compositions may also comprise additives, including inorganic salts, generally in the form of buffers, which allow the pH to be adjusted to a suitable range.

Process for Preparing Compounds

In another aspect, the present invention provides a process for preparing compounds of formula (I).

The compounds of formula I may be synthesized by reacting a compound of formula II $$H—\equiv—CH_2—O—L—SO_3^- \quad (II)$$

with a compound of formula III: $R_f$—I (III). The group $R_f$ is a $C_4$-$C_{10}$ alkyl substituted with 2m or (2m+1) fluoro atoms where m is the number of carbons in the alkyl backbone) in the presence of a radical initiator, followed by the addition of a strong base, to form a compound of formula (I). The reaction may be carried out in one or more solvents including acetone, methylethylketone, methylpropylketone, acetonitrile, water, and alcohols such as ethanol, isopropyl alcohol, n-butanol, etc. Examples of strong bases that may be used in the fluoroalkylation of a compound of formula II include LiOH, NaOH, and KOH.

Any suitable radical initiators known to one skilled in the art may be employed including chemical, UV, and heat initiators and methods disclosed in Dolbier, W. R. *Chem. Rev.* 1996, 96, 1557-1584, and Brace, N, O. *J. Fluorine Chem.* 1999, 93, 1-25. Examples of chemical initiators include, for example, azo initiators such as AlBN (azo-isobutyronitrile), hydroxymethanesulfinic acid sodium salt ($HOCH_2SO_2Na$—also called "Rongalite", sodium dithionite ($Na_2S_2O_4$), thiourea dioxide ($(NH_2)_2CSO_2$), metals (Fe, Cu, Zn, etc.) and metal salts such as CuCl/ethanolamine. Preferably the radical initiator is a chemical initiator, more preferably, an azo initiator or hydroxymethanesulfinic acid sodium salt, and most preferably AlBN or hydroxymethanesulfinic acid sodium salt. In certain embodiments, the radical initiator is 2,2'-azo-bis-2-methylpropionitrile, CuCl, dithionite thiourea dioxide, or sodium hydroxymethane sulfinate. The radical initiator is present in an amount sufficient to initiate the radical reaction between the fluoroalkylating agent and the alkenyl sulfate, preferably 10 mole % relative to the fluoroalkyl iodide, more preferably 5 mole %, most preferably 1 mole %.

The compound of $R_f$—I is a "fluoroalkylating agent" which is a molecule capable of forming a fluoroalkyl radical under suitable reaction conditions, e.g., $C_4F_9I$, $C_6F_{13}I$, $C_8F_{17}I$, $C_{10}F_{21}I$, etc.

Compounds of formula II may be formed by sulfating a compound of formula IV:

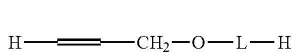

(IV)

with at least one sulfating agent. A "sulfating agent" refers to a compound that when reacted with a compound of formula IV results in a formula of compound II, under appropriate reaction conditions. Examples of sulfating agents include, but are not limited to sulfamic acid, sulfuric acid, chlorosulfonic acid, sulfur trioxide, or imidodisulfate. In certain embodiments, a sulfating agent is sulfamic acid.

The process of making a compound of formula I or II may further comprises purifying them to afford a solid form. Solid form includes crystalline, amorphous, semi-solid forms, or any other partially solid form. Purifying the alkenyl sulfate mixture may be performed by any suitable conditions known to one skilled in the art including for example solvent extraction, distillation, precipitation, or adsorption. Preferably, precipitation conditions are used for purifying the alkenyl sulfate mixture. The compound of formula I or II may be at least 90%, or 95%, or 98%, or 99% pure by weight.

Method of Extinguishing Fire

In one embodiment, a method of extinguishing a fire is provided. The method comprises applying to a fire a composition comprising a compound of formula (I). The compositions may be a foam, or a concentrate which upon dilution with water and aeration, produces a foam.

The foam or concentrate, upon dilution with water and aeration, produces an aqueous film-forming foam which is applied to a body of flammable liquid such as a spill or pool which is burning or subject to ignition. The foam extinguishes the burning liquid, prevents ignition. The foam provides a blanket to cover the fuel surface excluding air, and preventing further ignition of the liquid. Film-forming foam compositions are particularly desirable for extinguishing fires involving flammable fuels, such as gasoline, naphtha, diesel oils, hydraulic fluids, petroleum and other hydrocarbons. Film-forming foam compositions may also modified to be suitable for extinguishing fires involving polar solvent (including acetone, ethanol, and the like) by methods known to one skilled in the art, including those disclosed in U.S. Pat. Nos. 4,536,298 and 5,218,021.

The concentrates which when diluted with water and aerated produce a low density air-foam which quickly spreads on the surface of a body of hydrocarbon fuel, or other flammable liquid forming a blanket over the fuel or liquid. As the foam (on the surface of the flammable liquid) drains, a film is formed which, if disturbed or broken, tends to reform to seal off hot vapor emanating from the flammable liquid, thus extinguishing the fire. Although hydrocarbon surfactants may form a foam blanket, the flammable liquid vapors may wick through the foam and reignite. Foams comprising fluorosurfactants reduce the ability of the flammable liquid from wicking through the film and thereby prevent reignition.

As water under pressure passes through a fire hose, typically 3 percent by volume of the concentrate composition is inducted into the hose line by venturi effect to form a remixture (or "premix") of the concentrate diluted with water. The premix becomes aerated to produce a foam by use of an air-aspirating nozzle located at the outlet end of the hose. Additional equipment which can be used to produce and apply the aqueous air-foam of the invention is known to one skilled in the art or can be found in publications by the National Fire Protection Association.

In some aspects, the composition is a concentrate, which upon dilution with water and aeration, produces an aqueous film-forming foam. The method of extinguishing a fire may further comprise mixing the concentrate with water passing through a fire extinguishing hose in order to form a premixture; aerating the premixture as it passes through a hose or a nozzle attached thereto to produce an aqueous film-forming foam; and applying the aqueous film-forming foam to a fire, preferably a flammable liquid fire.

The composition can preferably be used in either the gaseous or the liquid state (or both), and any of the known techniques for introducing the composition to a fire can be utilized. For example, a composition can be introduced by streaming, by misting, or by flooding the composition onto a fire or hazard. The composition can optionally be combined with inert propellants, including, for example, nitrogen, argon, or carbon dioxide, to increase the rate of discharge of the composition from the streaming or flooding equipment utilized.

Preferably, the compositions are introduced into a fire or flame in an amount sufficient to extinguish the fire or flame. One skilled in the art will recognize that the amount of extinguishing composition needed to extinguish a particular hazard will depend upon the nature and extent of the hazard.

EXAMPLES

The following examples are offered to illustrate, but not to limit, the claimed invention.

Additionally, those skilled in the art will recognize that the molecules claimed in this patent may be synthesized using a variety of standard organic chemistry transformations.

Certain molecules claimed in this patent can exist in different enantiomeric and diastereomeric forms and all such variants of these compounds are within the scope of the invention.

In the descriptions of the syntheses that follow, some precursors were obtained from commercial sources. These commercial sources include Aldrich Chemical Co.

Compounds of the invention can be made by the methods and approaches described in the following experimental section, and by the use of standard organic chemistry transformations that are well known to those skilled in the art.

The compounds and others within the scope of this invention can be made and tested for activity using the following procedures.

Reagents and solvents used below can be obtained from commercial sources such as Aldrich Chemical Co. (Milwaukee, Wis., USA.

Sulfation Reactions. Sulfation of allyl alcohols and allyl alcohol alkoxylates can be carried out using a variety of sulfating agents (see Sandler & Karo, "Organic Functional Group Preparations", Volume III, Academic Press 1972). One of the safest and simplest procedures uses inexpensive sulfamic acid, with or without solvent, and with a small amount of added catalyst such as pyridine or tetramethyl urea.

Example 1

Allyl Sulfate, Sodium and Ammonium Salts

Allyl alcohol (17.4 g; 0.30 mole), sulfamic acid (29.1 g; 0.30 mole), and tetramethyl urea (0.5 g) were stirred vigorously in 40 ml of toluene and heated at reflux until the sulfamic acid had completely dissolved (approximately 2 hours). The mixture was allowed to stand without stirring at ambient temperature overnight, during which time the lower product layer solidified to a crystalline cake. This cake was separated from the toluene layer, rinsed once with an additional 40 ml of toluene, dissolved in 100 ml of hot ethanol, filtered to remove some insoluble material, and finally crystallized by slow addition of 200 ml of ether and ice cooling. The hygroscopic ammonium salt was filtered off, rinsed with a little ether, and quickly transferred to a vacuum oven for drying. Crystalline product (32 g.; 69% yield) melting at 77-79° C. was obtained sufficiently pure for use in subsequent reactions. (K. Nakano, Kogyo Kagaku Zasshi, 69: 1163 (1966) gave a m.p. of 72-74° C.) After recrystallizing several times from ethanol/ether a sample of this material melted at 86-87° C. NMR ($CD_3OD$): 5.98 (C═CH—, 1H, m); 5.34 ($H_2C$═C, 1H, d); 5.19 ($H_2C$═C—, 1H, d); 4.48 (C═C—$CH_2O$, 2H, d).

A sample of this product was converted to its sodium salt by dissolving in methanol containing an equivalent of sodium hydroxide and diluting with an equal volume of isopropanol. Ice cooling gave the sodium salt as large, flat crystalline plates.

After drying under vacuum, this material did not have a distinct melting point, but showed decomposition around 164° C.

Conversion of the sodium salt to the S-benzylisothiouronium salt gave a crystalline derivative (from water) with a sharp melting point of 85-86° C.

Example 2

Allyloxyethyl Sulfate, Sodium Salt

Allyloxyethanol (102.13 g; 1.0 mole), sulfamic acid (107 g; 1.1 mole), and pyridine (1 g) were stirred vigorously with a mechanical stirrer and heated at 100-105° C. until all the sulfamic acid had dissolved (approximately 3.5 hours). The resulting thick, brown syrup was cooled to room temperature, diluted with 1 L of isopropanol, and filtered through a bed of CELITE® to remove some insoluble material. Sodium hydroxide (41 g; 1.02 mole) dissolved in 300 ml of methanol was added to the isopropanol filtrate. Cooling in the refrigerator overnight gave the product as large, flat crystalline plates. The hygroscopic crystals were filtered, rinsed with isopropanol, and dried in a vacuum oven. A second crop of crystals was obtained by concentrating the filtrate on a rotary evaporator and cooling. In this way a total of 154 g (75% yield) of crystalline sodium salt was obtained.

Similar to Example 1 this salt had no distinct melting point, but decomposed >150° C.

NMR ($CD_3OD$): 5.90 (C═CH—, 1H, m); 5.28 ($H_2C$═C—, 1H, d); 5.16 ($H_2C$═C—, 1H, d); 4.12 (C—$CH_2OS$, 2H, t); 4.04 (C═C—$CH_2O$, 2H, d); 3.69 ($OCH_2$—COS, 2H, t).

This salt was also obtained by stirring 1.02 g (10 mmoles) of allyloxyethanol with 1.53 g (11 mmoles) of sulfur trioxide-trimethylamine complex in 2ml of toluene containing 2 drops of pyridine. After stirring at ambient for 4 hours, the white solids had dissolved leaving a clear colorless solution. NaOH (440 mg; 11 mmoles) in 5 ml of methanol was added and the solution evaporated to dryness. The white residual solid was recrystallized twice from methanol/isopropanol as above to give 1.0 g (49% yield) of white, crystalline plates.

Example 3

Diethylene Glycol Monoallylether Sulfate

Diethylene glycol monoallyl ether was prepared by reacting allyl bromide with excess diethylene glycol in THF-NaH (tetrahydrofuran-sodium hydride). The product was obtained in 82% yield after distillation. b.p.=96-99° C./7 mmHg.

Using the procedures given in Example 1 this alcohol was sulfated and its sodium salt obtained as an amorphous brown solid in 88% yield.

NMR ($CD_3OD$): 5.92 (C═CH—, 1H, m); 5.28 ($H_2C$═C, 1H, d); 5.16 ($H_2C$═C—, 1H, d); 4.13 (C—$CH_2OS$, 2H, t); 4.03 (C═C—$CH_2O$, 2H, d); 3.73 (O—$CH_2$—C, 2H, m); 3.66 (C—$CH_2O$, 2H, m); 3.60 ($OCH_2$—COS, 2H, m).

Example 4

Sulfation of Propoxylated Allyl Alcohol (1.6 Propoxy Groups/Mole)

Allyl alcohol propoxylate CAS (9042-19-7) (available as product no. 430374 from Aldrich Chemical Co.) was sulfated as for Example 1. After separating the toluene layer, the thick oily product layer was taken up in 1:1 methanol/isopropanol, filtered through CELITE®, and evaporated to a clear syrup (67% yield).

NMR ($CD_3OD$): 5.92 (C═CH—, 1H, m); 5.29 ($H_2C$═C, 1H, d); 5.17 ($H_2C$═C—, 1H, d); 4.02 (C═C—$CH_2O$, 2H, m); 3.76 (C—CHOS, 2.2H, d); 3.38 (O—$CH_2$—COS, 4.8H, m); 1.14 ($CH_3$—COS, 6.4H, m). NMR integration indicates around 2.2 propoxy groups/mole.

Example 5

$C_4F_9I$ Alkylation of Allyloxyethyl Sulfate-(E/Z)-2-(4,4,5,5,6,6,7,7,7-nonafluorohept-2-enyloxy)ethyl hydrogen sulfate 20.4 g (0.10 mole) of the allyloxyethyl sulfate (Na salt) from Example 2 was dissolved with 10 g (0.10 mole) $KHCO_3$ and 0.2 g of $Na_2SO_3$ in 100 ml water. To this was added 1 g (6 mmoles) of AIBN (2,2'-azobis-2-methylpropionitrile), 34.6 g (0.10 mole) of perfluorobutyl iodide, and 50 ml of isopropyl alcohol. The mixture was stirred vigorously and heated to reflux for 2 hours at which time a clear, one phase solution had formed.

The reaction was cooled to 60° C. and 0.4 g (0.010 mole) of NaOH was added to eliminate HI from the iodo intermediate. After holding at 60° C. for 2 hours, the clear reaction solution was cooled to ambient and pH adjusted to 7.5.

A sample of this solution was evaporated to dryness for analysis by NMR ($CD_3OD$).

$^{1}H$, 6.56 (C═CH—, 0.8H(E), m); 6.44 (C═CH—, 0.2H (Z), m); 6.04 ($C_4F_9CH$═, 0.8H(E), q); 5.75 ($C_4F_9CH$═, 0.2H(Z), q); 4.25 (C═C—$CH_2O$, 2H, m); 4.17 (C—$CH_2OS$, 2H, t); 3.77 ($CH_2$—COS, 2H, t).

$^{19}F$: −127.4 (γ-$CF_2$); −125.8 (β-$CF_2$) −113.3 (α-(E)$CF_2$); −109.3 (α-(Z)$CF_2$); −83.1 (ω-$CF_3$).

Example 6

$C_4F_9I$ Alkylation of Propoxylated Allyl Alcohol Sulfate

The sulfate salt from example 4 was perfluoroalkylated by the same procedure as Example 5. A sample was purified by column chromatography (silica gel; ethyl acetate/methanol 1:1) for NMR analysis in $CD_3OD$.

$^1$H, 6.56 (C═CH—, 0.8H(E), m); 6.42 (C═CH—, 0.2H (Z), m); 6.06 ($C_4F_9CH$═, 0.8H(E), q); 5.75 ($C_4F_9CH$═, 0.2H(Z), q); 4.42 (C═C—$CH_2O$, 2H, m); 3.76 (C—CHOS, 2H, t); 3.42 ($OCH_2$—COS, 2H, t); 1.14 ($CH_3$—COS).

$^{19}$F: −127.5 (γ-$CF_2$); −126.1 (β-$CF_2$) −113.5 (α-(E)$CF_2$); −109.3 (α-(Z)$CF_2$); −83.1 (ω-$CF_3$).

Example 6A

$C_6F_{13}$I Alkylation of Propoxylated Allyl Alcohol Sulfate

This product was prepared using the sulfate salt from Example 4 and $C_6F_{13}$I according to the procedure of Example 5.

Example 7

$C_6F_{13}$I Alkylation of Allyl Sulfate-(E/Z)-4,4,5,5,6,6,7,7,8,8,9,9,9-tridecafluoronon-2-enyl hydrogen sulfate 15.5 g (0.10 mole) of allyl sulfate ($NH_4$ salt), 10 g (0.10 mole) $KHCO_3$, and 0.85 g (5.5 mmoles) of $HOCH_2SO_2Na$ (sodium hydroxymethane sulfinate) (Rongalite) were dissolved in 100 ml of water. 44.6 g (0.10 mole) of perfluorohexyl iodide and 50 ml of isopropanol were added and the reaction mixture heated to reflux with vigorous stirring. Within a few minutes a clear, single-phase solution had formed which was held at reflux for 2 hours. After cooling to 60° C., 4.0 g (0.10 mole) of NaOH was added and held for another 2 hours to complete the dehydroiodination. The clear reaction solution was cooled to ambient and pH adjusted to 7.5.

A sample of this solution was evaporated to dryness for analysis by NMR.

NMR ($CD_3OD$). $^1$H, 6.63 (C═CH—, 0.8H(E), m); 6.49 (C═CH—, 0.2H(Z), m); 6.09 ($C_6F_{13}CH$═, 0.8H(E), q); 5.79 ($C_6F_{13}CH$═, 0.2H(Z), q); 4.68 (C═C—$CH_2O$, 2H, m). $^{19}$F: −127.8 (ε-$CF_2$); −124.9 (δ-$CF_2$) −124.3 (γ-$CF_2$); −123.1 (β-$CF_2$); −113.1 (α-(E)$CF_2$); −109.1 (α-(Z)$CF_2$); −82.86 (ω$CF_3$).

Example 8

$C_6F_{13}$I Alkylation of Allyloxyethyl Sulfate-(E/Z)-2-(4,4,5,5,6,6,7,7,8,8,9,9,9-tridecafluoronon-2-enyloxy)ethyl hydrogen sulfate Crystalline allyloxyethyl sulfate (Na salt) from the preparation shown in example 2 was perfluoroalkylated using the procedure of example 7. A sample of the product was salted out of the reaction solution and crystallized from ethanol for NMR analysis.

NMR ($CD_3OD$). $^1$H, 6.56 (C═CH—, 0.8H(E), m); 6.43 (C═CH—, 0.2H(Z), m); 6.04 ($C_6F_{13}CH$═, 0.8H(E), q); 5.75 ($C_6F_{13}CH$═, 0.2H(Z), q); 4.16 (C—$CH_2OS$, 2H, t); 4.13 (C═C—$CH_2O$, 2H, m); 3.78 ($CH_2$—COS, 2H, t). $^{19}$F: −127.8 (ε-$CF_2$); −124.9 (δ-$CF_2$) −124.3 (γ-$CF_2$); −123.1 (β-$CF_2$); −113.1; (α-(E)$CF_2$); −109.1 (α-(Z)$CF_2$); −82.85 (ω$CF_3$

Example 9

$C_8F_{17}$I Alkylation of Allyloxyethyl Sulfate

Crystalline allyloxyethyl sulfate (Na salt) from the preparation shown in example 2 was perfluoroalkylated using the procedure of example 7 and $C_8F_{17}$I to produce 2-(4,4,5,5,6,6,7,7,8,8,9,9,10,10,11,11,11-heptadecafluoroundec-2-enyloxy)ethyl hydrogen sulfate.

Example 10

$C_6F_{13}$I Alkylation of Diethylene Glycol Monoallylether Sulfate

The monoallylether sulfate from Example 3 was perfluoroalkylated according to the procedure described in Example 7 to produce 2-(2-(4,4,5,5,6,6,7,7,8,8,9,9,9-tridecafluoronon-2-enyloxy)ethoxy)ethyl hydrogen sulfate.

Example 11

$C_6F_{13}$I Alkylation of Ethoxylated Allyl Alcohol Sulfate

Polyethoxylated allyl alcohol sulfate (available from Rhodia as Rhodapex CL-910, containing approximately 10 ethoxy groups) was perfluoroalkylated according to the procedure described in Example 7. The $C_6F_{13}$I alkylation of ethoxylated allyl alcohol sulfate that contained 10 ethoxy groups would be named as 34,34,35,35,36,36,37,37,38,38,39,39,39-tridecafluoro-3,6,9,12,15,18,21,24,27,30-decaoxatetracont-32-enyl hydrogen sulfate.

Surface Tension and Foam Quality Data for Alpha Olefin Sulfates

| Product of Example | Surface Tension (dynes/cm)[1] | Foam Expansion[2] | 50% Drain Time (minutes) |
|---|---|---|---|
| 7 | 19 | 4.1 | 4:05 |
| 5 | 35 | 4.3 | 3:31 |
| 8 | 17 | 4.2 | 5:36 |
| 9 | 15 | 3.6 | 6:15 |
| 10 | 17 | 4.0 | 4:45 |
| 11 | 30 | 3.5 | 2:52 |
| 6 | 20 | 4.4 | 3:23 |
| 6A | 17 | 4.7 | 5:30 |
| 2-(4,4,5,5,6,6,7,7,8,8,9,9,9-tridecafluorononyloxy) ethanesulfonate | 21[3] | 3.8 | 3:05 |
| 2-(3,3,4,4,5,5,6,6,7,7,8,8,8-tridecafluorooctyloxy) ethanesulfonate | 20[4] | — | — |

[1] Surface tension was measured with a Kruss DSA100 drop volume tensiometer at 1000 ppm concentration in deionized water.
[2] Foam expansion is the ratio of foam volume divided by its original liquid volume. Foam was generated from 100 ml of a deionized water solution of each compound prepared to contain a fluorine concentration of 0.05 w/v %. Foam generation was performed in a kitchen blender for 60 seconds at high speed, and the volume measured in a graduated cylinder. 50% drain time (minutes:seconds) is the time for 50 ml of the original 100 ml volume to drain to the bottom of the cylinder.
[3] Prepared by hydrogenation of the iodo intermediate.
[4] Surface tension taken from U.S. Pat. No. 3,952,075.

Surface tension is a property that defines the spreading coefficient of one liquid over a second immiscible liquid. For a foamable solution, a positive spreading coefficient is indicative of a material that will spread over the fuel in question. During this process a very thin film is formed at the fuel/water interface. The formation of a film in conjunction with the foam generated during discharge, works to seal the fuel surface during the fire extinguishing process.

The time which passes between the time the blender has stopped and when the foam is converted to liquid is the drain time.

It is therefore intended that the foregoing detailed description be regarded as illustrative rather than limiting, and that it be understood that it is the following claims, including all equivalents, that are intended to define the spirit and scope of this invention.

What is claimed is:

1. A fire extinguishing composition comprising:
at least one solvent; and
a first fluorosurfactant of formula (I)

$$[R_f—\equiv—CH_2—O—L—SO_3^-]_x\,M \qquad (I)$$

where
L is absent, $C_1$-$C_{10}$ alkylene-O—, $(—CH_2CH_2O—)_n$, $(—CH_2CH(CH_3)O—)_n$, or $(—CH_2CH(OH)CH_2O—)_n$;
n is an integer from 1 to 10;
$R_f$ is a $C_4$-$C_{10}$ alkyl group substituted with 2m or (2m+1) fluoro atoms where m is the number of carbons in the alkyl backbone;
M is an alkali metal cation, an alkaline earth metal cation, ammonium cation, a $C_1$-$C_4$ mono-substituted ammonium cation, a $C_1$-$C_4$ di-substituted ammonium cation, a $C_1$-$C_4$ tri-substituted ammonium cation, or a $C_1$-$C_4$ tetra-substituted ammonium cation; and
x is an integer selected from 1 or 2, and corresponds to the valency of M.

2. The composition of claim 1, further comprising a hydrocarbon surfactant; and a second fluorosurfactant.

3. The composition of claim 1, wherein said solvent is selected from the group consisting of water, iso-propyl alcohol, t-butyl alcohol, glycol, butyl carbitol, and hexylene glycol.

4. A method of extinguishing a fire comprising:
applying to said fire a composition comprising:
at least one solvent; and
a compound of formula I $$[R_f—\equiv—CH_2—O—L—SO_3^-]_xM \qquad (I)$$

where
L is absent, $C_1$-$C_{10}$ alkylene-O—, $(—CH_2CH_2O—)_n$, $(—CH_2CH(CH_3)O—)_n$, or $(—CH_2CH(OH)CH_2O—)_n$;
n is an integer from 1 to 10;
$R_f$ is a $C_4$-$C_{10}$ alkyl group substituted with 2m or (2m+1) fluoro atoms where m is the number of carbons in the alkyl backbone;
M is an alkali metal cation, an alkaline earth metal cation, ammonium cation, a $C_1$-$C_4$ mono-substituted ammonium cation, a $C_1$-$C_4$ di-substituted ammonium cation, a $C_1$-$C_4$ tri-substituted ammonium cation, or a $C_1$-$C_4$ tetra-substituted ammonium cation; and
x is an integer selected from 1 or 2, and corresponds to the valency of M.

5. The method of claim 4, wherein the composition further comprises a hydrocarbon surfactant; and a second fluorosurfactant.

6. The method of claim 4, wherein $R_f$ is $C_4F_9$, $C_6F_{13}$, or $C_8F_{17}$.

7. The method of claim 4, wherein said solvent is selected from the group consisting of water, iso-propyl alcohol, t-butyl alcohol, glycol, butyl carbitol, and hexylene glycol.

8. A compound of formula (I):

$$[R_f—\equiv—CH_2—O—L—SO_3^-]_xM \qquad (I)$$

where
L is absent, $C_1$-$C_{10}$ alkylene-O—, $(—CH_2CH_2O—)_n$, $(—CH_2CH(CH_3)O—)_n$, or $(—CH_2CH(OH)CH_2O—)_n$;
n is an integer from 1 to 10;
$R_f$ is a $C_4$-$C_{10}$ alkyl group substituted with 2m or (2m+1) fluoro atoms where m is the number of carbons in the alkyl backbone;
M is an alkali metal cation, an alkaline earth metal cation, ammonium cation, a $C_1$-$C_4$ mono-substituted ammonium cation, a $C_1$-$C_4$ di-substituted ammonium cation, a $C_1$-$C_4$ tri-substituted ammonium cation, or a $C_1$-$C_4$ tetra-substituted ammonium cation; and
x is an integer selected from 1 or 2, and corresponds to the valency of M.

9. The compound of claim 8, wherein M is an alkali metal cation selected from the group consisting of a potassium, lithium, and sodium cation, and x is 1.

10. The compound of claim 8, wherein M is a magnesium cation, and x is 2.

11. The compound of claim 8, wherein M is an ammonium cation, a $C_1$-$C_4$ mono-substituted ammonium cation, a $C_1$-$C_4$ di-substituted ammonium cation, a $C_1$-$C_4$ tri-substituted ammonium cation, or a $C_1$-$C_4$ tetra-substituted ammonium cation and x is 1.

12. The compound of claim 9, wherein $R_f$ is a $C_4$-$C_{10}$ alkyl containing (2m+1) fluoro atoms where m is the number of carbons in the alkyl backbone.

13. The compound of claim 12, wherein $R_f$ is $C_4F_9$, $C_6F_{13}$, or $C_8F_{17}$.

14. The compound of claim 13, wherein L is $(—CH_2CH_2O—)_n$.

15. The compound of claim 14, wherein n is 0, 1 or 2.

16. The compound of claim 8, wherein said compound is selected from the group consisting of:
2-(4,4,5,5,6,6,7,7,7-nonafluorohept-2-enyloxy)ethyl hydrogen sulfate;
4,4,5,5,6,6,7,7,8,8,9,9,9-tridecafluoronon-2-enyl hydrogen sulfate;
2-(4,4,5,5,6,6,7,7,8,8,9,9,9-tridecafluoronon-2-enyloxy) ethyl hydrogen sulfate;
2-(4,4,5,5,6,6,7,7,8,8,9,9,10,10,11,11,11-heptadecafluoroundec-2-enyloxy)ethyl hydrogen sulfate; and
34,34,35,35,36,36,37,37,38,38,39,39,39-tridecafluoro-3,6,9,12,15,18,21,24,27,30-decaoxatetracont-32-enyl hydrogen sulfate.

* * * * *

UNITED STATES PATENT AND TRADEMARK OFFICE

CERTIFICATE OF CORRECTION

PATENT NO. : 8,524,104 B1
APPLICATION NO. : 12/548530
DATED : September 3, 2013
INVENTOR(S) : Jeffrey D. Michael It is certified that error appears in the above-identified patent and that said Letters Patent is hereby corrected as shown below:

On the Title Page

Left column, item (73), replace "Ansul, Incorporated, Marinette, WI (US)" with --Tyco Fire Products LP, Lansdale, PA (US)--.

Signed and Sealed this
First Day of April, 2014

Michelle K. Lee
*Deputy Director of the United States Patent and Trademark Office*